United States Patent [19]

Harreus et al.

[11] Patent Number: 5,200,532

[45] Date of Patent: Apr. 6, 1993

[54] PREPARATION OF 2,2-DISUBSTITUTED-2,3-DIHYDROBENZOFURANS

[75] Inventors: Albrecht Harreus, Ludwigshafen; Bernd Wolf, Fussgoenheim; Jochen Wild, Ruppertsberg, all of Fed. Rep. of Germany

[73] Assignee: BASF Aktiengesellschaft, Ludwigshafen, Fed. Rep. of Germany

[21] Appl. No.: 750,347

[22] Filed: Aug. 27, 1991

[30] Foreign Application Priority Data

Aug. 31, 1990 [DE] Fed. Rep. of Germany ....... 4027573

[51] Int. Cl.$^5$ .............................................. C07D 307/79
[52] U.S. Cl. ....................................................... 549/462
[58] Field of Search ........................................ 549/462

[56] References Cited

U.S. PATENT DOCUMENTS 3,821,256  6/1974  Vollrath et al. .
4,298,615  11/1981 Schwarz et al. .
4,857,516  8/1989  Terao et al. ........................ 514/100

FOREIGN PATENT DOCUMENTS 0023637  11/1981 European Pat. Off. .
345593   12/1989 European Pat. Off. .
2108932   8/1972 Fed. Rep. of Germany .
2255581   3/1974 Fed. Rep. of Germany .

OTHER PUBLICATIONS

Barton et al., J. Chem. Soc., pp. 4393-4398 (1958).
Kirk-Othmer-Encyclopedia of Chem. Technology-3rd Ed., John-Wiley & Sons, N.Y., vol. 15, pp. 659-669.
Houben-Weyl, Methoden der organischen Chemie, vol. 6/3, p. 620 ff. (1965).
Arduini et al., Synthesis, 1984, p. 950 ff.
Casnati et al, J. Org. Chem., 48(21), 3783-3787 (1983).
Martini et al, J. Org. Chem., 35(9) 2904-2907 (1970).
Laan et al, Chemistry and Industry, (11) 354-355 (1989).
Gervais et al., Tetrahedron, 35(6) 745-752 (1979).

Primary Examiner—Bernard Dentz
Attorney, Agent, or Firm—Herbert B. Keil

[57] ABSTRACT

A process for the preparation of a 2,3-dihydrobenzofuran I

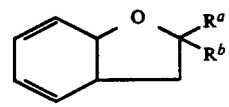

or a derivative thereof, where $R^a$ and $R^b$ are C-organic radicals, involves reacting a 2-hydroxybenzyl alcohol II

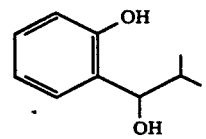

in the presence of an acidic ion exchanger resin and in the presence of an inert dehydrating substance. Novel 2,3-dihydrobenzofurans Ia, 2-acylphenols IVa and 2-hydroxybenzyl alcohols IIa, a process for their preparation, and their use as intermediates are also described.

8 Claims, No Drawings

PREPARATION OF 2,2-DISUBSTITUTED-2,3-DIHYDROBENZOFURANS

The present invention relates to a novel process for the preparation of a 2,2-disubstituted 2,3-dihydrobenzofuran I

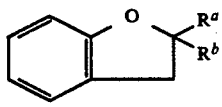

or a derivative thereof, where $R^a$ and $R^b$, independently of one another, are C-organic radicals, by reacting a 2-hydroxybenzyl alcohol II

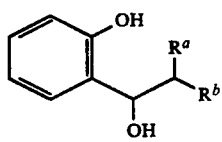

or a derivative thereof in an inert organic solvent in the presence of an acidic ion exchanger resin.

The present invention also relates to 2,2-disubstituted 2,3-dihydrobenzofurans of the formula Ia

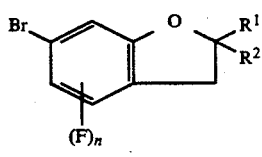

where
R$^1$ and R$^2$, independently of one another, are $C_1$–$C_6$-alkyl, and
n is 0 or 1,
to a process for the preparation thereof, and to 2-acylphenols of the formula

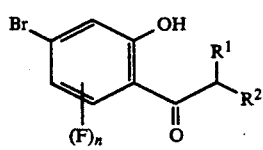

and 2-hydroxybenzyl alcohols of the formula IIa

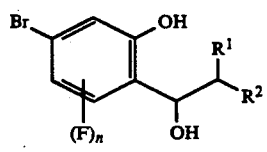

where the substituents and the index are as defined above, as intermediates.

The preparation of dihydrobenzofurans is known in principle. The most frequent procedure used is the synthesis of the heterocyclic ring by Claisen rearrangement of o-allylphenyl ethers and subsequent cyclization of the ortho-allylphenols obtained (Houben-Weyl, Methoden der organischen Chemie, Volume 6/3, pages 620 ff. (1965); German Laid-Open Application DE-OS 2108932). However, the latter reactions have significant disadvantages for obtaining the substituted dihydrobenzofurans of the formula I, in particular the poor regioselectivity and the poor availability of the allylating reagents required.

It is also known that 2,2-disubstituted 2,3-dihydrobenzofurans can be obtained by reacting the corresponding 2-hydroxybenzyl alcohols in toluene in the presence of catalytic amounts of Amberlyst® 15, an acidic ion exchanger resin containing sulfonic acid groups (Arduini et al., Synthesis, 1984, pp. 950 ff.).

However, the described synthesis in the presence of acidic ion exchangers is unsuitable for economical use in industry since, due to the risk of polymerization of starting materials and intermediates, the reaction must be carried out at high dilutions. In addition to the problem this causes of treating and disposing of large amounts of solvents and the problem of high energy consumption, this process only gives low space-time yields.

As has already been disclosed in the literature, the cyclization of 2-hydroxybenzyl alcohols proceeds in two steps:

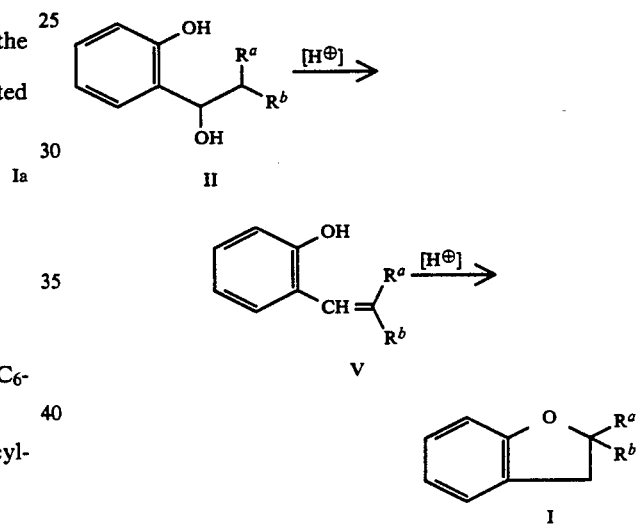

As can be seen from the reaction scheme, both the elimination (1st step) and the cyclization (2nd step) are catalyzed by protons. Since both the hydroxybenzyl alcohol II and the intermediate 2-vinylphenol V can polymerize with one another and with themselves, long reaction times and high concentrations of these substances in the reaction medium result in side reactions and thus in losses in yield of the 2,3-dihydrobenzofuran I.

It is an object of the present invention to provide an economically acceptable process for the preparation of 2,2-disubstituted 2,3-dihydrobenzofurans.

We have found that this object is achieved by a process for the preparation of the 2,2-disubstituted 2,3-dihydrobenzofuran I

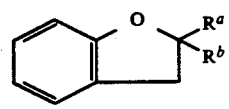

or a derivative thereof, where $R^a$ and $R^b$ are as defined above, by reacting a 2-hydroxybenzyl alcohol II

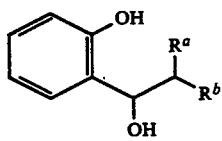

or a derivative thereof in an inert organic solvent in the presence of an acidic ion exchanger resin, which comprises carrying out the reaction in the presence of an inert dehydrating substance.

In addition, the novel 2,2-disubstituted 2,3-dihydrobenzofurans of the formula Ia defined at the outset, a process for their preparation, novel 2-acylphenols of the formula Va and novel 2-hydroxybenzyl alcohols of the formula IIa have been found as intermediates.

In the process according to the invention, the addition of an inert dehydrating substance causes the hydroxybenzyl alcohol II to be converted into the 2-vinylphenol V more quickly. In this way, the reaction time and thus the probability of side reactions are reduced.

In addition, the reaction rate is affected by the amount of acidic catalyst employed. The ideal ratio between catalyst and hydroxybenzyl alcohol II is dependent on the type and position of the substituents on the phenyl moiety of the benzyl alcohol II and must be determined individually in each case.

A paper published in Synthesis, 1984, has already examined the suitability of silica gel or acidic or neutral alumina as a cyclization catalyst. Although said substances combine both acidic (or in the latter case neutral) properties and dehydrating properties, the authors only achieved a yield of less than 50% using these catalysts.

However, reaction of the alcohols of the formula II or the benzyl alcohol III used by Arduini et al. under the same concentration conditions but without addition of desiccant results in only partial conversion of the alcohols II or the olefin intermediate does not react and additional side reactions occur.

Suitable inert dehydrating substances, which are necessary according to the invention for the cyclization, are, in particular, inorganic desiccants, such as magnesium sulfate, sodium sulfate, anhydrous calcium sulfate (for example Drierite ®) and calcium chloride, preferably molecular sieves having a pore size of from 3 Å to 10 Å, particularly preferably from 3 to 4 Å. These desiccants are generally used in at least amounts in which, in accordance with their water-absorption capacity, are able to absorb one mol of water per mol of 2-hydroxybenzyl alcohol.

The maximum amount of desiccant is determined by process-technical and economic considerations; an optimum must be found in each case taking into account the following points:
 the rate of water removal is directly dependent on the surface area of the desiccant and thus on the amount and grain size of the desiccant;
 since the desiccant exists as a solid phase in the reaction medium, it should be ensured that it does not prevent sufficient convection of the reaction mixture;
 since the desiccant preferably has a large surface area, it should be ensured that a loss in yield during processing, which may occur, for example, due to inclusion of the product in the desiccant residue, is avoided or at least minimized;
 in cases where the desiccant cannot be regenerated without losses, economic aspects could be taken into account.

If the desiccant used is molecular sieve, the following points have proven advantageous:
 the molecular sieve should have a pore size of at least 3 Å and not more than 10 Å, in particular from 3 Å to 4 Å;
 the amount of molecular sieve of from 3 Å to 4 Å should, in accordance with the abovementioned considerations, be from 50 g to 500 g, in particular from 100 g to 300 g, per mol of 2-hydroxybenzyl alcohol.

The concentration of the 2-hydroxybenzyl alcohol in the reaction medium can be varied within a broad range in the process according to the invention; here too, the optimum must be determined taking into account various points of view:
 the amount of solvent must be at least sufficient to dissolve the 2-hydroxybenzyl alcohol employed;
 in addition, the amount of solvent is dependent on the minimum amount of desiccant and ion exchanger to be used, and convection of the reaction medium must be ensured;
 where the solvent cannot be regenerated without losses, economic aspects could be taken into account.

In general, the solvent is used in an amount of from 0.5 l to 10 l per mol of the 2-hydroxybenzyl alcohol II (corresponding to from 0.1 to 2 mol/l of II), in particular from 1 l to 3 l per mol of II (corresponding to from 0.3 to 1 mol/l of II).

In view of the fact that it is expedient to use the smallest possible amount of solvent, it is advisable to introduce the minimum amount of solvent necessary together with the necessary amounts of catalyst and desiccant, and to add the 2-hydroxybenzyl alcohol II successively. A reaction carried out in this way is also suitable for reducing the risk of polymerization of the starting materials or for preventing polymerization entirely (dilution principle).

Suitable inert organic solvents are aliphatic and aromatic, halogenated or unhalogenated hydrocarbons, such as dichloromethane, chloroform, carbon tetrachloride, cyclohexane, benzene, toluene, xylene or mixtures thereof, preferably toluene or benzene.

Suitable catalysts are, in general, highly acidic ion exchanger resins, for example Amberlyst ® 15, which was mentioned in the introduction, but also other Amberlyst ® grades and Lewatit ® and Amberlite ®.

The amount of catalyst to be used depends essentially on the degree of charging of this catalyst with protons, the amount of 2-hydroxybenzyl alcohol II and the type of substituents in the phenyl moiety of the alcohol.

It is usual to employ from 0.001 to 1.0 mol equivalents of protons, preferably from 0.01 to 0.5 mol equivalents of protons, per mol of the alcohol.

The reaction temperature may be varied within a broad range from room temperature (25° C.) to the boiling point of the solvent or solvent mixture. The maximum temperature generally depends on the stability of the precursors and intermediates (compounds II and V).

The reaction is usually carried out at an adequate rate at 25° C., although the compounds can generally be heated to 180° C. without spontaneous decomposition occurring. The reaction is preferably carried out at from 30° C. to 150° C., in particular from 60° C. to 120° C.

The reaction mixture is worked up and the products are isolated in a conventional manner by first removing the catalyst and desiccant from the reaction mixture and subsequently isolating the product from the resultant reaction solution by crystallization, chromatography or distillation.

The process according to the invention is suitable for the preparation of a 2,2-disubstituted 2,3-dihydrobenzofuran I or a substituted derivative thereof from the corresponding 2-hydroxybenzyl alcohol, in particular of the formula II'

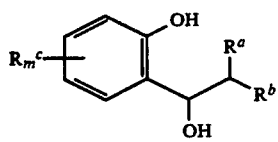

where
- $R^a$ and $R^b$, independently of one another are C-organic radicals, such as alkyl and aryl, it being necessary for these substituents to be of such a nature that they stabilize a positive partial charge on the carbon atom to which they are bonded; experience hitherto has not shown any effect on the process of substituents on these C-organic radicals which are inert under the reaction conditions;
- $R^c$ is a substituent which is inert under the reaction conditions, such as one of the C-organic radicals mentioned above, or alkenyl or alkynyl, which may be bonded directly or via a hetero atom, such as oxygen, sulfur or nitrogen; $R^c$ is alternatively halogen, cyano, carboxyl or nitro; and
- m is 0, 1, 2 or 3, it being possible for the radicals $R^c$ to be different from one another if m is 2 or 3; the value of m only affects the process inasmuch as high steric hindrance due to bulky radicals or radicals in the 2- or 5-position of the phenol may reduce the reaction rate.

$R^a$, $R^b$ and $R^c$ are preferably:
alkyl having up to six carbon atoms, in particular $C_1$–$C_4$-alkyl, such as methyl, ethyl, propyl, 1-methylethyl, butyl, 1-methylpropyl or 2-methylpropyl;
alkenyl having up to six carbon atoms, in particular $C_2$–$C_4$-alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl or 2-methyl-2-propenyl;
alkynyl having up to six carbon atoms, in particular $C_2$–$C_4$-alkynyl, such as ethynyl, 1-propynyl, 2-propynyl, 1-butynyl, 2-butynyl, 3-butynyl or 1-methyl-2-propynyl; aryl, in particular phenyl.

The abovementioned C-organic radicals may be bonded directly or via hetero atoms, such as oxygen, sulfur or nitrogen.

Halogen atoms, such as fluorine, chlorine, bromine and iodine, in particular fluorine, chlorine and bromine, or cyano, carboxyl or nitro groups are also possible.

The index m generally has a value of 0, 1, 2 or 3, preferably 0, 1 or 2, it being possible for the radicals to be different from one another if m is 2 or 3.

The abovementioned radicals may themselves be interrupted by hetero atoms, such as nitrogen, oxygen or sulfur, or carry further inert radicals, such as halogen, nitro, sulfonyl, arylsulfonyl or carboxyl.

The 2,2-disubstituted 2,3-dihydrobenzofurans I and derivatives thereof, which are more readily accessible by the process according to the invention, are used, for example, as intermediates in the preparation of pharmaceuticals, dyes and crop-protection agents.

With respect to their use as intermediates for crop-protection agents, particular preference is given to the novel 2,2-disubstituted 2,3-dihydrobenzofurans of the formula Ia

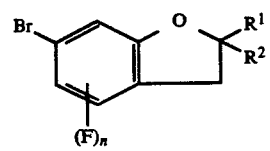

where
- $R^1$ and $R^2$, independently of one another, are $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, and
- n is 0 or 1.

These compounds Ia are obtained, for example, by rearranging an appropriate phenol ester of the formula IIIa in a conventional manner by a Fries shift in the presence of a Lewis acid, subsequently reducing the resultant 2-acylphenol of the formula IVa in a conventional manner, and cyclizing the resultant 2-hydroxybenzyl alcohol of the formula IIa in a conventional manner to give the 2,2-disubstituted 2,3-dihydrobenzofuran Ia.

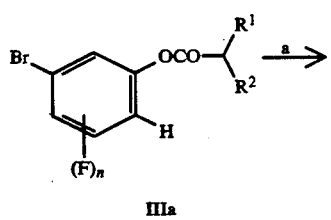

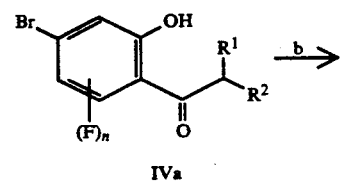

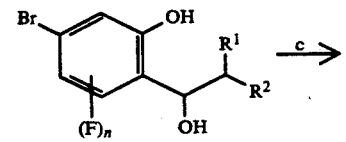

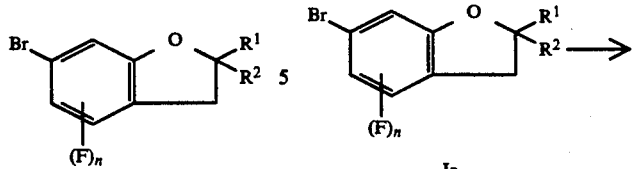

Reactions a, b and c are in detail carried out as follows:
a) Rearrangement of the Phenol Ester by a Fries Shift (Houben-Weyl, Methoden der organischen Chemie, Volume VII/2a, Pages 379 ff.; Briggs et al., Can. J. Chem. 34, 851 (1956))

The reaction is generally carried out at from 80° to 200° C., preferably from 100° to 160° C.

Suitable Lewis acids are preferably aluminum trichloride and tin tetrachloride, in particular aluminum trichloride.

The compounds of the formula IIIa are themselves obtainable by esterification methods similar to those known from the literature, for example reaction of an appropriate 3-bromophenol with an acid chloride in the presence of a base, such as pyridine or triethylamine, in an inert organic solvent, for example dichloromethane.
b) Reduction of the Acylphenol (Houben-Weyl, Vol. IV, 1d, pp. 1 ff.)

Particularly suitable reducing agents are hydrides, such as lithium aluminum hydride and sodium borohydride.

The reduction is generally carried out at from −10° C. to the boiling point of the solvent, preferably from 0° to 100° C.

Examples of suitable solvents are alcohols, such as methanol, ethanol, isopropanol, propanol, butanol and isobutanol, in particular methanol, ethanol and isopropanol, or ethers, such as diethyl ether, t-butyl methyl ether, dioxane and tetrahydrofuran.
c) Cyclization of the 2-Hydroxybenzyl Alcohol The cyclization is carried out either by one of the processes described in the literature cited in the introduction or, particularly advantageously, by the process according to the invention.

The 2-acylphenols of the formula IVa and the 2-hydroxybenzyl alcohols of the formula IIa are likewise novel. They are valuable intermediates for economical and simple preparation of pharmaceuticals, dyes and crop-protection agents.

With respect to their use as intermediates for the synthesis of crop-protection agents, the radicals and index in the formulae IIa and IVa are generally and particularly as defined above for the novel 2,2-disubstituted 2,3-dihydrobenzofurans of the formula Ia.

The novel 2,2-disubstituted 2,3-dihydrobenzofurans of the formula Ia are preferably used to synthesize pesticides, in particular pyrethroids. In this context, they are first converted into the benzaldehydes V in a conventional manner, subsequently reduced to benzyl alcohols VI and esterified with an acid which is customary for pyrethroids to give the active ingredients VII.

This synthesis is summarized below:

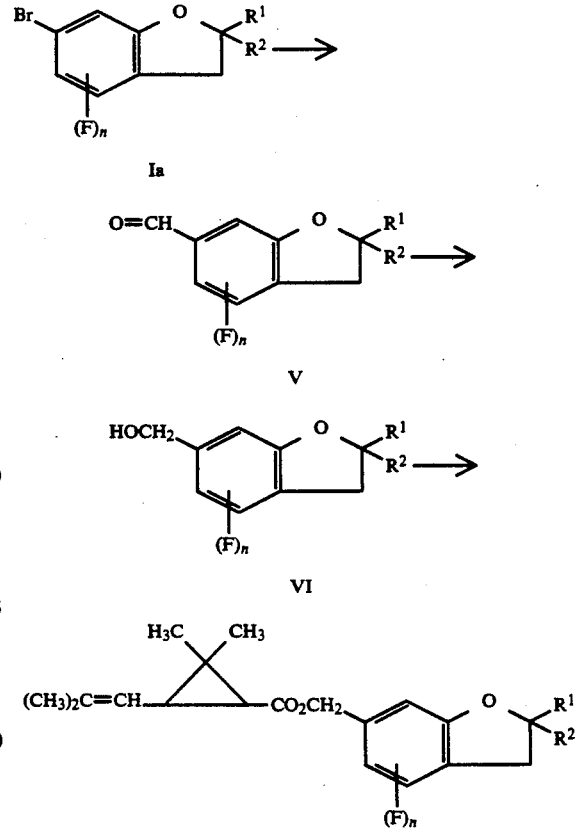

Active ingredients of this type are described, for example, in DE-A 21 08 932, DE-A 22 55 581 and EP-A 23 637.

The corresponding 5-chloro-substituted 2,3-dihydrobenzofurans which are known from the literature are not suitable for this synthesis since they cannot be converted into the corresponding benzaldehydes V.

Experimental Part

1. Investigations of the Cyclization of the Compounds II to Give the 2,2-Disubstituted 2,3-Dihydrobenzofurans I The appropriate 2-hydroxybenzyl alcohol (BA) II, the acidic ion exchanger (CAT), the solvent (S) and, if desired, the desiccant (D) were mixed in the ratios given in Table 1 and stirred at the appropriate temperature (T).

The course of the experiment was assessed by carrying out the following determinations:
*) A 2 ml sample was taken from the reaction mixture and filtered through kieselguhr, and the filtrate was analyzed by gas chromatography on a capillary column without washing the filtration residue. The solvent content was set at 0%.
**) The reaction batch was filtered through kieselguhr with suction, the residue was washed with dichloromethane, the filtrate was evaporated, and the crude product was analyzed by gas chromatography on a capillary column; dichloromethane was used to dilute the sample. The unisolated yield was determined from the content of I and the weight of crude product. In addition, the crude product was investigated by $^1$H—NMR spectroscopy.

TABLE 1

| No. | BA II | T (°C.) | S | D | Amount of BA II employed (mol) | BA II (mol) | CAT (mol of H+) | D (g) |
|---|---|---|---|---|---|---|---|---|
| V-0 | i | 80 | T | — | 0.01 | 0.1 | 0.01 | — |
| V-1 | i | 80 | T | — | 0.1 | 0.1 | 0.01 | — |
| V-2 | i | 80 | T | — | 0.1 | 0.4 | 0.04 | — |
| E-1 | i | 80 | T | MS | 0.1 | 0.4 | 0.04 | 200 |
| V-3 | ii | 80 | T | — | 0.04 | 0.5 | 0.05 | — |
| E-2 | ii | 80 | T | MS | 0.04 | 0.5 | 0.05 | 200 |
| E-3 | ii | 80 | T | MS | 0.04 | 0.5 | 0.2 | 200 |
| E-5 | ii | 80 | T | MgSO$_4$ × H$_2$O | 0.04 | 0.5 | 0.2 | 200 |
| E-6 | ii | e | DM | MS | 0.04 | 0.5 | 0.05 | 200 |
| E-7 | ii | 25 | T | MS | 0.04 | 0.5 | 0.2 | 200 |
| E-8 | ii | 40 | T | MS | 0.04 | 0.5 | 0.2 | 200 |
| E-9 | ii | 65 | T | MS | 0.04 | 0.5 | 0.2 | 200 | i: 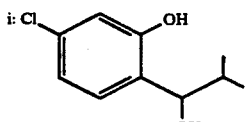

ii: 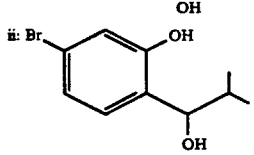

T: toluene
DM: dichloromethane
MS: molecular sieve 3 Å
e: boiling point of the reaction mixture
CAT: Amberlyst 15

The dependency of the process on the concentration of 5-chloro-2-(1-hydroxymethylpropyl)phenol (BA II) and on the addition of desiccant was investigated in an illustrative manner (experiments V-1, V-2 and E-1 in Table 1-1) by variation in comparison to the general procedure given by Arduini et al. (Synthesis (1984), 950, Method A, p. 952, corresponds to Table 1, experiment V-0). It is apparent that complete conversion over 78 hours can only be achieved by a ten-fold increase in the size of the original batch. If the concentration of the starting material is increased by a factor of 4, the yield of I drops considerably (comparison of the 24 hour values of V-1 and V-2), but can be significantly increased again by carrying out the reaction, for example, in the presence of molecular sieve as desiccant (E-1).

TABLE 1-1

Effect of concentration
(Standardized to 1,000 ml of toluene, T = 80° C., BA II = i)

| | BA II (mol) | CAT (mol of H+) | D (g) | t (h) | GC analysis (% of I) |
|---|---|---|---|---|---|
| V-1 | 0.1 | 0.1 | — | 24 | 84 |
| | | | | 78 | 92 |
| V-2 | 0.4 | 0.04 | — | 24 | 61 |
| E-1 | 0.4 | 0.04 | 200 | 24 | 77 |

TABLE 1-2

Effect of the desiccant
(Standardized to 1,000 ml of toluene, T = 80° C., BA II = ii)

| | BA II (mol) | CAT (mol of H+) | D (g) | t (h) | Unisolated yield** (% of I) |
|---|---|---|---|---|---|
| V-3 | 0.5 | 0.05 | — | 7 | 52 |
| E-2 | 0.5 | 0.05 | 200 | 7 | 77 |

TABLE 1-2-continued

Effect of the desiccant
(Standardized to 1,000 ml of toluene, T = 80° C., BA II = ii)

| | BA II (mol) | CAT (mol of H+) | D (g) | t (h) | Unisolated yield** (% of I) |
|---|---|---|---|---|---|
| E-3 | 0.5 | 0.2 | 200 | 7 | 90 |

TABLE 1-3

Comparison of solvents and desiccants
(Standardized to 1,000 ml of solvent, 200 g of SD, BA II = ii)

| | BA II (mol) | CAT (mol of H+) | D | S | T (°C.) | t h | GC analysis (% of I) |
|---|---|---|---|---|---|---|---|
| E-2 | 0.5 | 0.05 | MS | toluene | 80 | 4 | 73 |
| | | | | | | 7 | 83 |
| E-6 | 0.5 | 0.05 | MS | DM | e | 4 | 60 |
| | | | | | | 7 | 63 |
| E-3 | 0.5 | 0.2 | MS | toluene | 80 | 4 | 86 |
| | | | | | | 7 | 91 |
| E-5 | 0.5 | 0.2 | MgSO$_4$ × H$_2$O | toluene | 80 | 4 | 77 |
| | | | | | | 7 | 82 |

TABLE 1-4

Effect of temperature on the process
(Standardized to 1,000 ml of toluene, 200 g of MS, BA II = ii)

| | BA II (mol) | CAT (mol of H+) | T (°C.) | t (h) | Unisolated yield** (% of I) |
|---|---|---|---|---|---|
| E-9 | 0.5 | 0.2 | 65 | 7 | 64 |
| E-3 | 0.5 | 0.2 | 80 | 7 | 90 |

2. Preparation of the Novel 2,2-Disubstituted 2,3-Dihydrobenzofurans Ia

EXAMPLE 1

3-Bromophenyl Isobutyrate

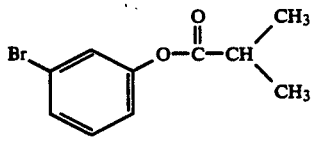

561 g (7.1 mol) of pyridine and then 682 g (6.4 mol) of isobutyryl chloride are added dropwise at 25° C. to 1,004 g (5.8 mol) of 3-bromophenol in 600 ml of dichloromethane, during which the reaction mixture warms to 50° C. The mixture is stirred at 25° C. for a further 18 hours, and the pyridine hydrochloride is then removed using dichloromethane. The organic phase is washed first with water, then with dilute hydrochloric acid and finally again with water. All the low-boiling components are subsequently removed by distillation at 10 mbar and a bath temperature of 40° C.

The 3-bromophenyl isobutyrate which remains is reacted further without additional purification. Yield: 1,326 g (94%). $^1$H—NMR data, see Table 1.

The following examples are obtained in a similar manner.

EXAMPLE 2

5-Bromo-2-(1-Methylethylcarbonyl)Phenol

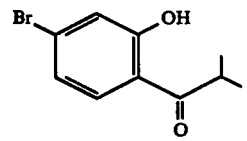

320 g (2.4 mol) of aluminum chloride are added in portions at −10° C. to 388.7 g (1.6 mol) of the 3-bromophenyl isobutyrate from Example 1, and the mixture is allowed to warm to 25° C. and then heated at 100° C. until no further gas is evolved (about 1 hour). The mixture is allowed to cool, and 500 ml of dry 1,2-dichloroethane are then slowly added at from 50° to 60° C., giving a homogeneous solution. The cooled solution is hydrolyzed by careful pouring into ice water. The mixture is acidified using hydrochloric acid until the precipitate from the hydrolysis has dissolved to give a clear solution, and the organic phase is isolated, dried and subjected to fractional distillation under reduced pressure.

The fractions obtained in the boiling range from 75° to 80° C. at 0.1 mbar are recrystallized from petroleum ether.

Yield: 47%, m.p.: 55° to 57° C.

$^1$H—NMR and $^{13}$C—NMR data, see Table 2.

The examples shown in Table B are obtained in a similar manner:

TABLE A

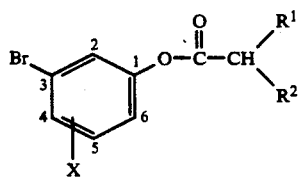

| No. | X | R$^1$ | R$^2$ | Yield. % | 250-MHz-$^1$H-NMR (CDCl$_3$); δ (ppm) |
|---|---|---|---|---|---|
| 1.001 | H | —CH$_3$ | —CH$_3$ | 96 | 1.3(d, 6H) |
| | | | | | 2.8(m, 1H) |
| | | | | | 7.0–7.4(4H) |
| 1.002 | H | —CH$_3$ | —CH$_2$—CH$_3$ | 92 | 1.0(t, 3H) |
| | | | | | 1.1(d, 3H) |
| | | | | | 1.45–1.9(2m, 2H) |
| | | | | | 2.6(m, 2H) |
| | | | | | 6.8–7.4(m, 4H) |
| 1.003 | H | —CH$_2$—CH$_3$ | —CH$_2$—CH$_3$ | 98 | 1.1(d, 6H) |
| | | | | | 1.5–1.9(m, 4H) |
| | | | | | 2.4–2.6(m, 1H) |
| | | | | | 6.9–7.4(m, 4H) |
| 1.004 | 4-F | —CH$_3$ | —CH$_3$ | 85 | 1.3(d, 6H) |
| | | | | | 2.8(m, 1H) |
| | | | | | 6.9–7.4(m, 3H) |

TABLE B

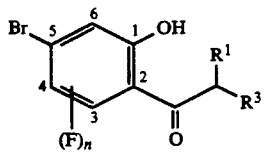

| No. | (F)$_n$ | R$^1$ | R$^2$ | Yield % | Physical Properties | 250 MHz-$^1$H-NMR (CDCl$_3$) or 67.9 MHz-$^{13}$C-NMR (CDCl$_3$); δ (ppm) | |
|---|---|---|---|---|---|---|---|
| 2.001 | — | —CH$_3$ | —CH$_3$ | 47 | m.p. 54–55° C. | $^1$H:[1]<br>1.1(d, 6H):<br>3.5(m, 1H)<br>6.95–7.2(2d, 2H)<br>7.58(d, 1H)<br>12.6(s, 1H) | $^{13}$C:[1]<br>163.5 (C-1);<br>121.7 (C-2)<br>130.4 (C-3)<br>121.8 (C-4)<br>130.7 (C-5)<br>116.9 (C-6) |
| 2.002 | — | —CH$_3$ | —CH$_2$CH$_3$ | 68 | b.p. 88–90° C. (0.1 mbar) | $^1$H:<br>0.94(t, 3H)<br>1.2(d, 3H)<br>1.5(m, 1H)<br>1.8(m, 1H)<br>3.35(m, 1H)<br>7.0(dd, 1H)<br>7.15(d, 1H)<br>7.6(d, 1H)<br>12.8(s, 1H) | $^{13}$C:<br>163.7 (C-1)<br>122.0 (C-2)<br>130.5 (C-3)<br>122.4 (C-4)<br>130.8 (C-5)<br>117.8 (C-6) |
| 2.003 | — | —CH$_2$CH$_3$ | CH$_2$CH$_3$ | 36 | b.p.: = 99–100° C. (0.1 mbar) | 200 MHz-$^1$H-NMR (CDCl$_3$)<br>0.9(t, 3H)<br>1.5–2.0(2m, 4H)<br>3.25(m, 1H)<br>7.05(dd, 1H)<br>7.2(d, 1H)<br>7.65(d, 1H)<br>12.8(s, 1H) | |
| 2.004 | 4-F | —CH$_3$ | —CH$_3$ | | | 1.25(d, 6H)<br>3.46(m, 1H)<br>7.25(m, 1H)<br>7.55(d, 1H)<br>13.3(s, 1H) | |

[1] selected signals

EXAMPLE 3

5-Bromo-2-(1-Hydroxy-2-Methylpropyl)Phenol

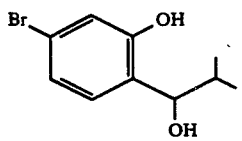

40.8 g (1.08 mol) of sodium borohydride are added to 1,100 ml of isopropanol, and 261 g (1.08 mol) of the 5-bromo-2-(1-methylethylcarbonyl)phenol from Example 2, dissolved in 300 ml of isopropanol, are added dropwise. The mixture is subsequently stirred at 80° C. for 2 hours and cooled, the solvent is removed, and the residue obtained is taken up in methyl tert-butyl ether (MTBE) and ice water. The mixture is extracted by shaking, the organic phase is separated off, and the aqueous phase is back-extracted several times with MTBE. The combined organic phases are dried and freed from solvent at 20° C. under reduced pressure. The residue obtained in this way is recrystallized from n-hexane, an optimum yield being obtained by cooling the mixture to −40° C. for crystallization.

Yield: 94%.
m.p.: 75° to 78° C.
Spectroscopic data see Table C
The examples from Table C were obtained in a similar manner.

TABLE C

| No. | (F)$_n$ | R$^1$ | R$^2$ | Yield % | Physical Properties | Spectroscopic data 200 MHz-$^1$H-NMR (CDCl$_3$); (ppm) |
|---|---|---|---|---|---|---|
| 3.001 | — | —CH$_3$ | —CH$_3$ | 94 | m.p.: 75–78° C. | 0.85(d, 2H) 1.03(d, 2H)<br>2.08(m, 1H) 2.7(broad s. 1H)<br>4.5(d, 1H) 6.77(d, 1H)<br>6.95(dd, 1H); 7.01(d, 1H).<br>8.3(breites s. 1H) |
| 3.002 | — | —CH$_3$ | —CH$_2$—CH$_3$ | 88 | — | (Diastereomer mixture 1:1)<br>0.6–1.4(m, 9H, OH, 2 × CH$_3$, CH$_2$) |

TABLE C-continued

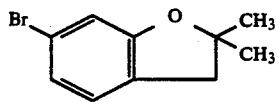

| No. | (F)$_n$ | R$^1$ | R$^2$ | Yield % | Physical Properties | Spectroscopic data 200 MHz-$^1$H-NMR (CDCl$_3$); (ppm) |
|---|---|---|---|---|---|---|
| 3.003 | — | —CH$_2$CH$_3$ | —CH$_2$—CH$_3$ | | oil | 1.5–1.9(m, 1H, —CHMeEt) 4.4–4.7(2d, 1H, —CH—OH) 6.6–7.0(m, 3H) 0.7–1.0(2t, 6H) 1.0–1.7(m, 5H) 4.65(d, 1H) 6.75(d, 1H) 6.8–7.0(m, 2H) 8.8(breites s, 1H) |

EXAMPLE 4

6-Bromo-2,2-Dimethyl-2,3-Dihydrobenzofuran 4001

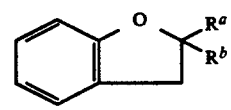

122.6 g (0.5 mol) of the 5-bromo-2-(1-hydroxy-2-methylpropyl)phenol from Example 3 are dissolved in 1,000 ml of dry toluene. 200 g of molecular sieve (3 Å) and 42.6 g (0.2 mol equivalents of H⊕) of Amberlyst 15 are added, the mixture is heated to 80° C. and stirred for 24 hours.

The mixture is filtered through kieselguhr with suction, and the filtrate is freed from solvent and fractionated under reduced pressure.

Crude product: 111 g, 84% pure according to GC analysis ( 82% of theory).

The dihydrobenzofurans listed in Table D were obtained in a similar manner:

TABLE D

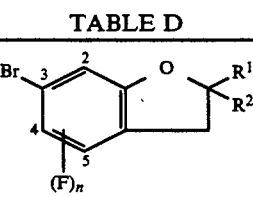

| No. | (F)$_n$ | R$^1$ | R$^2$ | Physical Properties | 270 MHz $^1$H-NMR (CDCl$_3$); δ (ppm) |
|---|---|---|---|---|---|
| 4.001 | — | —CH$_3$ | —CH$_3$ | b.p.: = 65–69° C. (0,3 mbar) | 1.45(s, 6H) 2.9(s, sH) 6.8–7.0(m, 3H) |
| 4.002 | — | —CH$_3$ | —CH$_2$CH$_3$ | b.p.: = 75° C. (0,1 mbar) | 0.91(t, 3H): 1.35(s, 3H). 1.7(q, 2H): 2.9(dd, 2H), 6.8–7.0(m, 3H) |
| 4.003 | — | —CH$_2$CH$_3$ | —CH$_2$CH$_3$ | b.p.: = 78–80° C. (0,15 mbar) | 0.9(t, 6H) 1.72(g, 4H) 2.92(s, 2H) 6.8–7.0 (m, 3H) |

We claim:

1. A process for the preparation of a 2,2-disubstituted 2,3-dihydrobenzofuran I

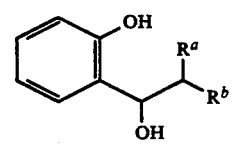

or a derivative thereof, where R$^a$ and R$^b$, independently of one another, are C-organic radicals, by reacting a 2-hydroxybenzyl alcohol II or a derivative thereof in an inert organic solvent in the presence of an acidic ion exchange resin, the improvement which comprises carrying out the reaction in the presence of an inert inorganic desiccant.

2. A process as defined in claim 1, wherein the inert inorganic desiccant is a molecular sieve.

3. A process as defined in claim 1, wherein the inert inorganic desiccant is used in an amount in which, it is able to absorb at least one mol of water per mol of 2-hydroxybenzyl alcohol.

4. A process as defined in claim 2, wherein from 100 g to 500 g of molecular sieve are used per mol of 2-hydroxybenzyl alcohol.

5. A process as defined in claim 1, wherein the solvent is used in an amount of from 0.5 l to 10 l per mol of 2-hydroxybenzyl alcohol.

6. A process as defined in claim 1, wherein the solvent is used in an amount of from 1 l to 3 l per mol of 2-hydroxybenzyl alcohol II.

7. A process as defined in claim 2, wherein the inert inorganic dessicant is used in an amount which, in accordance with its absorption capacity for water, is able to absorb at least one mol of water per mol of 2-hydroxybenzyl alcohol.

8. A process as defined in claim 7, wherein the solvent is used in an amount of from 0.5 l to 10 l per mol of 2-hydroxybenzyl alcohol.

* * * * *